US012272439B1

(12) United States Patent
Soon-Shiong et al.

(10) Patent No.: US 12,272,439 B1
(45) Date of Patent: Apr. 8, 2025

(54) DISTRIBUTED LEDGER FOR MEDICAMENT ADMINISTRATION TRACKING

(71) Applicant: ImmunityBio, Inc., Culver City, CA (US)

(72) Inventors: Patrick Soon-Shiong, Los Angeles, CA (US); Nicholas J. Witchey, Laguna Hills, CA (US)

(73) Assignee: ImmunityBio, Inc., Culver City, CA (US)

( * ) Notice: Subject to any disclaimer, the term of this patent is extended or adjusted under 35 U.S.C. 154(b) by 0 days.

(21) Appl. No.: 18/656,535

(22) Filed: May 6, 2024

(51) Int. Cl.
*G16H 20/13* (2018.01)
*G07C 9/00* (2020.01)

(52) U.S. Cl.
CPC ......... *G16H 20/13* (2018.01); *G07C 9/00182* (2013.01); *G07C 9/00896* (2013.01)

(58) Field of Classification Search
None
See application file for complete search history.

(56) References Cited

U.S. PATENT DOCUMENTS

| | | |
|---|---|---|
| 8,676,509 B2 | 3/2014 | De La Torre-Bueno |
| 9,262,719 B2 | 2/2016 | Soon-Shiong |
| 10,050,959 B2 | 8/2018 | Soon-Shiong et al. |
| 10,093,964 B2 | 10/2018 | Mehta |
| 10,340,038 B2 * | 7/2019 | Witchey ............... H04W 12/02 |
| 10,811,140 B2 | 10/2020 | Toumazou et al. |
| 10,885,173 B2 | 1/2021 | Witchey et al. |
| 10,923,215 B2 | 2/2021 | Witchey et al. |
| 11,017,897 B2 | 5/2021 | Soon-Shiong |

(Continued)

FOREIGN PATENT DOCUMENTS

WO     2009139984 A2     11/2009

OTHER PUBLICATIONS

Rahul G. Ingle, et al., Prefilled dual chamber devices (DCDs)—Promising high-quality and convenient drug delivery system, https://doi.org/10.1016/j.ijpharm.2021.120314, 9 pages.

(Continued)

*Primary Examiner* — Robert A Sorey
(74) *Attorney, Agent, or Firm* — Maschoff Brennan; Elaine K. Lee; Andrew A. Noble

(57) ABSTRACT

An autonomous tracking system receives a request to administer a patient-specific therapeutic comprising a scanned identifier associated with a labeled dual chamber device (DCD) including a first chamber having one or more lyophilized components, a second chamber having a reconstitution buffer, and a locking mechanism for controlling access to the DCD chambers. A tracking engine queries an administration database based on the scanned identifier to find a notarized ledger associated with the DCD and retrieves a blockchain entry comprising a first distributed ledger transaction identifying the one or more lyophilized components and a digital token associated with an owner of the labeled DCD. After the owner is authenticated, a second distributed transaction is created identifying the one or more lyophilized components as being authorized for administration to the patient. In response, autonomous access to the one or more lyophilized components unlocks the locking mechanism to administer the medication.

32 Claims, 6 Drawing Sheets

(56) References Cited

U.S. PATENT DOCUMENTS

| | | |
|---|---|---|
| 11,048,788 B2 | 6/2021 | Witchey et al. |
| 11,210,383 B2 | 12/2021 | Witchey et al. |
| 11,321,652 B1* | 5/2022 | Mahmood ............... G16H 40/67 |
| 11,386,985 B2* | 7/2022 | Witchey ................. G16H 10/60 |
| 11,455,385 B2 | 9/2022 | Witchey et al. |
| 11,785,002 B2 | 10/2023 | Soon-Shiong et al. |
| 11,785,004 B2 | 10/2023 | Soon-Shiong et al. |
| 11,798,244 B1 | 10/2023 | Witchey et al. |
| 11,880,824 B1 | 1/2024 | Witchey et al. |
| 11,894,109 B1 | 2/2024 | Niazi et al. |
| 11,899,768 B2 | 2/2024 | Witchey et al. |
| 11,954,627 B2* | 4/2024 | Mahmood ............... G16H 10/40 |
| 11,977,530 B2 | 5/2024 | Soon-Shiong et al. |
| 11,983,157 B2 | 5/2024 | Soon-Shiong et al. |
| 12,052,240 B2 | 7/2024 | Soon-Shiong et al. |
| 2008/0235055 A1 | 9/2008 | Mattingly et al. |
| 2016/0200462 A1* | 7/2016 | Kriheli ............. G06Q 10/06316 700/214 |
| 2022/0374807 A1* | 11/2022 | Mahmood ............... G16H 40/67 |
| 2024/0131115 A1 | 4/2024 | Liu et al. |

OTHER PUBLICATIONS https://openchainproject.org, 2024, accessed Sep. 9, 2024, 6 pages.

Intel's Sawtooth Lake, https://github.com/hyperledger-archives/sawtooth-core/tree/0-7/extensions/bond, 2017, accessed Sep. 9, 2024, 2 pages.

DNA Nudge, https://www.dnanudge.com/pages/the-science-bit, 2024, accessed September 9, 8 pages.

Ethereum, https://ethereum.org/en/, website last updated Sep. 4, 2024, accessed Sep. 9, 2024, 15 pages.

Hyper Ledger Project, https://www.hyperledger.org/, 2024, accessed Sep. 18, 2024, 2 pages.

U.S. Appl. No. 18/100,544 to Witchey et al. titled, "Efficient Computer-Based Indexing Via Digital Tokens, Systems, Methods, and Apparatus," filed Jan. 23, 2023.

U.S. Appl. No. 17/590,291 to Witchey et al. titled "Token-Based Digital Private DataMethods, and Apparatus," filed Feb. 1, 2022.

* cited by examiner

DISTRIBUTED LEDGER FOR MEDICAMENT ADMINISTRATION TRACKING

TECHNICAL FIELD

The technical field is digital tracking technologies for tracking delivery of patient therapeutics.

BACKGROUND

The background description includes information that may be useful in understanding the systems and methods described herein. It is not an admission that any of the information provided herein is prior art, or that any publication specifically or implicitly referenced is prior art.

The advent of personalized medicine has allowed patient-specific therapeutics to be developed that are specifically tailored to treat individual patients. For example, biological material may be obtained from a patient, provided to a manufacturer of a patient-specific therapeutic, and delivered to the patient for administration. For example, a patient-specific cancer therapeutic such as CAR T-cells may be engineered to express a chimeric antigen receptor, wherein the starting materials comprise immune cells (e.g., T-cells) obtained from a patient. The engineered CAR T-cells may be administered to the patient from which the biological material was obtained. In other cases, a neoepitope or neoantigen may be determined from analysis of the tumor cell, and an antibody-based therapeutic may be generated based on this information. In still other cases, viral or yeast-based vaccines may be designed and manufactured for administration to a patient to treat or prevent a particular type of cancer or other viral-related disease.

As personalized medicine is specifically tailored to an individual, it is important to ensure that mix-ups do not occur during any part of this process, beginning with obtaining a biological sample from an individual, through manufacturing a personalized therapeutic, and ending with delivery and administration of the therapeutic to the correct patient at a point of care. Delivery of a therapeutic to a patient other than to whom the therapy is tailored to may have adverse side effects (e.g., triggering an anaphylactic response, etc.), may fail to effectively treat the disease, and may potentially expose the patient to other diseases (e.g., diseases present in the patient from which the biological material was obtained).

Personalized medicine and other patient-specific therapeutics may often utilize drug delivery systems such as prefilled dual chamber devices (DCDs). DCDs are combination products containing freeze-dried drug and diluent in two separate chambers of the device. Advantages of DCDs over traditional drug delivery systems include accurate dosing, easy handling, seal integrity, and high stability. DCDs such as Vetter Lyo-Ject, LyoTwist, and Mix Jet provide instant acting and safe delivery (i.e., free of needle-stick injuries and airborne bacterial contaminants). DCDs can significantly improve patient compliance by allowing the patient to self-administer the medication by, for example, easily applying pressure to the end plunger first to initiate mixing and dissolving of the freeze-dried powder, and then allowing self-injection to occur. DCDs may also improve long term biopharmaceutical stability by storing medicaments in freeze-dried form before administration, and are therefore becoming more popular, especially for unstable biopharmaceutical products. Some DCDs are glue free to eradicate the risk of interaction with drug product and cannot be reused which makes it safe for disposal. The development of DCDs for a drug and flush solution instead of a catheter appears to help facilitate good clinical practices in many hospitals, as it helps avoid patient complications such as phlebitis or infection due to catheter use.

DCDs thus provide significant advantages over conventional injectables that involve vials and ampoules, as these cannot be used to administer lyophilized components without significant medical staff time involvement, and associated risk for spillage and contamination (e.g., pouring, mixing, and/or reconstituting medicaments by hand). DCDs may also move toward individualized treatment regimens that may be done by the patient at home without medical staff involvement, thus saving medical staff time and patient medical expenses, as well as improving patient compliance and quality of life. Further information about DCDs is available in the article by Rahul G. Ingle and Wei-Jie Fang, Prefilled dual chamber devices (DCDs)—Promising high-quality and convenient drug delivery system, International Journal of Pharmaceutics 597 (2021) 120314 (See URL doi.org/10.1016/j.ijpharm.2021.120314) the contents of which are incorporated herein by reference in its entirety.

Typically, patient-specific therapeutics are extrinsically labeled. For example, patient therapeutics may be labeled with extrinsic information (e.g., a patient's name, a bar code, etc.) affixed to its container. However, patient therapeutics being processed through a workflow (e.g., by a technician, etc.) may be mislabeled and/or mixed-up during manufacturing and processing. This may result in improper manufacturing of the patient-specific therapeutic (e.g., if workflows are switched, etc.) and/or may result in administration of the wrong therapeutic to a patient.

Examples of biological tracking systems are provided in the art. For example, U.S. Pat. No. 8,676,509 to De La Torre-Bueno entitled "System for Tracking Biological Samples", filed Nov. 13, 2002, provides real-time tracking of biological samples from collection through storage. Samples are associated with unique bar code identifiers that link to processing steps at various workstations. Such an approach aids in reducing possible processing errors with respect to managing tissue slides. However, the system still requires significant manual processing to tag the samples, and therefore, mix-ups are still possible.

As another example, U.S. Patent Application Publication No. US 2008/0235055 to Mattingly et al. entitled "Laboratory Instrumentation Information Management and Control Network", filed Jun. 13, 2007, discusses forming a harmonized specimen identifier from a case identifier of a patient and a specimen identifier. The harmonized specimen identifier represents a combination of identifiers arranged in a defined format, where the various identifiers aid in tracking a specimen at different points in a workflow.

More recently, blockchain technology has been proposed for use with supply chain tracking. A blockchain represents blocks of data that are linked together by cryptographic technology. Each block includes, among other things, data, and a cryptographic hash of a previous block. The cryptographic hash serves as a link to the previous block. As such, the blocks form a chain of blocks (e.g., a blockchain) linked via cryptographic hash. The data in each block is secured (e.g., against unauthorized modifications, etc.) because any change alters all subsequent blocks. Generally, a distributed computing architecture is used to manage the blockchain. This architecture can involve multiple computer nodes. Each computer node can store a block of the blockchain, and the computer nodes implement one or more protocols to communicate and validate blocks.

Various blockchain technologies are available including Microsoft's Confidential Consortium (CoCo), enterprise-level blockchain approaches such as openchain (see URL www.openchain.org) and Ethereum, and Intel's Sawtooth Lake (See URL intelledger.github.io/0.7/introduction.html), a distributed ledger platform that implements data models and transaction language using one or more transaction families.

However, all these approaches are geared towards tracking the container in which the patient therapeutic and/or biological sample is placed, and mix-ups are still possible. Thus, there remains a considerable need for improved tracking and verification systems to reduce or eliminate medication errors and mix-ups during processing and administration of personalized patient therapeutics and medications.

SUMMARY

Embodiments of the disclosed invention comprise a database, tracking chain, and tracking engine directed to the linkage of information via a distributed ledger, block chain or other form of notarized ledger, wherein said information pertains to one or more patients, diagnosis of said patients, prescription of one or more drugs to said patients, drug information, drug administration to the patient, and therapeutic outcome to the patient. The drug information may include one or more of manufacturing information, lyophilization information, storage instructions and tracking information, shipping instructions, and tracking data, point of care information, and reconstitution information.

Embodiments of the disclosed invention may be used with a variety of drugs, including but not limited to: (1)N-803 and at least one antibody, or (2)N-803 and Bacillus Calmette-Guérin (BCG), all individual components of which may be stored lyophilized in vials and reconstituted using a prefilled dual chamber device (DCD). The at least one antibody may include commercially (clinically) available checkpoint inhibitor antibodies in some embodiments. In one embodiment, the DCD should have at least one chamber for a reconstitution buffer, and at least one chamber for a lyophilized biological agent. In some embodiments, the DCD may be used with multiple, interchangeable vials, whereby the antibody to be administered with the N-803 resides in one or more capsules loaded on to the syringe (DCD) in tandem. Thus, in such embodiments, multiple lyophilized agents get solubilized in the same syringe (DCD) with the same reconstitution buffer and are administered in one shot to the patient. Such embodiments are flexible, and the patient diagnosis and prescription information, manufacturing, shipping, storage, administration, and therapeutic outcome are all readily tracked and recorded, ensuring fidelity of the administered medications to the clinician's prescription for the patient.

In some embodiments, the at least one antibody or BCG may be used in combination with N-803 (nogapendekin alfa inbakicept) known by the trade name Anktiva™. In some embodiments, N-803 comprises a complex of an interleukin-15 (IL-15) superagonist mutant and a dimeric IL-15 receptor a/Fc fusion protein., a solid tumor, urothelial/bladder carcinoma, In some embodiments, N-803 is useful for enhancing an immune response against a neoplasia (e.g., a glioblastoma, prostate cancer, hematological cancer, B-cell neoplasms, multiple myeloma, B-cell lymphoma, Hodgkin's lymphoma, acute myeloid leukemia, chronic lymphocytic leukemia, cutaneous T-cell lymphoma, T-cell lymphoma, melanoma, lung cancer, renal cell carcinoma, breast cancer, gastric and esophageal cancer, head and neck cancer, colorectal cancer, ovarian cancer, non-small cell lung carcinoma, B cell non-Hodgkin lymphoma, and squamous cell head and neck carcinoma) or an infection (e.g., a viral infection with human immunodeficiency virus).

In some embodiments, various devices, systems, structures, and methods are disclosed for autonomously tracking and administering medicaments. A tracking system receives a request for administering a medication to a patient, the request comprising at least one scanned identifier associated with a labeled dual chamber device (DCD), wherein the labeled DCD comprises a first chamber having one or more lyophilized components, a second chamber having a reconstitution buffer therein, and a locking mechanism for controlling access to at least one of the first chamber and the second chamber. A tracking engine queries an administration database based on the scanned identifier to find a notarized ledger associated with the labeled DCD, and retrieves a blockchain entry comprising a first distributed ledger transaction identifying: i) the one or more lyophilized components within one or more vials of the DCD, ii) a patient-specific therapeutic, and iii) a digital token associated with an owner of the labeled DCD. After an owner of the labeled DCD is authenticated using the digital token and the patient-specific therapeutic is validated, a second distributed transaction is created identifying the one or more lyophilized components as being authorized for administration to the patient. In response, autonomous access to the one or more lyophilized components transitions the locking mechanism from a locked state to an unlocked state with respect to at least one of the first chamber and the second chamber such that the patient-specific therapeutic can be administered to the patient.

Various objects, features, aspects, and advantages of the inventive subject matter will become more apparent from the following detailed description of preferred embodiments, along with the accompanying drawing figures in which like numerals represent like components.

BRIEF DESCRIPTION OF THE DRAWINGS

For the purposes of illustration only, several aspects of embodiments of the invention are described by reference to the following figures.

Figure 1A:
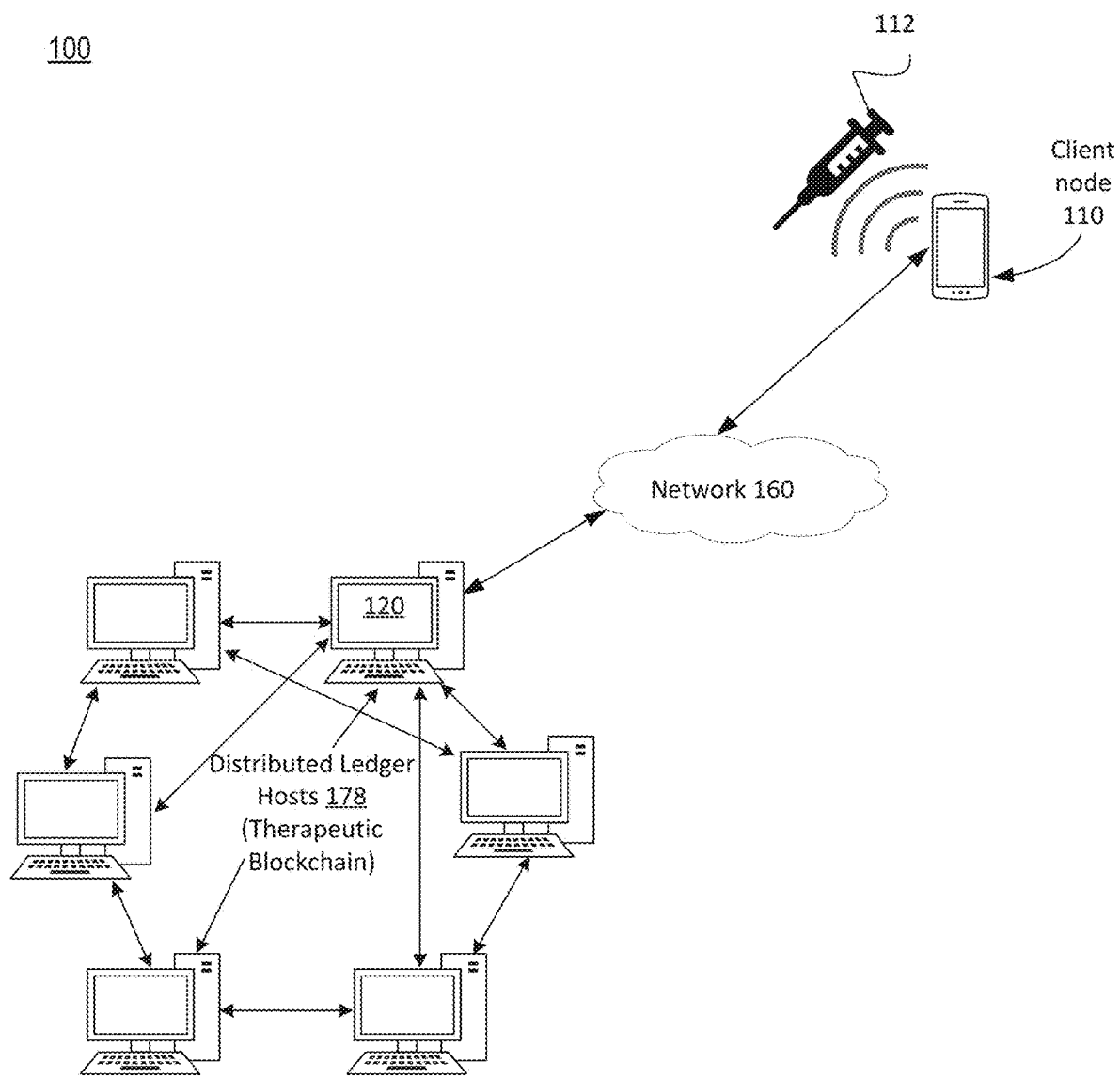
FIG. 1A illustrates a block diagram of an exemplary distributed computer system according to an embodiment of the present disclosure.

While the invention is described with reference to the above drawings, the drawings are intended to be illustrative, and other embodiments are consistent with the spirit, and within the scope, of the invention.

DETAILED DESCRIPTION

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, PLA, PLD, FPGA, etc.). The software instructions preferably configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network; a circuit switched network; cell switched network, or other type of network.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, when a system, engine, module, device, server, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory thereby forming a structure having specific purpose. It is understood that the user of "configured to" or "programmed to" (or similar language) are not to be construed to invoke interpretation under 35 USC 112(f).

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Embodiments of the present invention may be configured for use with pharmaceutical compositions comprising N-803 for use as a therapeutic as discussed above in the Summary, and in further detail below and in co-pending and co-owned U.S. patent application Ser. No. 18/394,409 and its related patent applications, each of which are incorporated herein by reference in its entirety. In one aspect, N-803 is administered systemically, for example, formulated in a pharmaceutically acceptable buffer such as physiological saline. Preferable routes of administration include, for example, instillation into the bladder, subcutaneous, intravenous, intraperitoneal, intramuscular, intranasally, topically, or intradermal injections that provide continuous, sustained levels of the composition in the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia or infection. Generally, amounts will be in the range of those used for other agents used in the treatment of other diseases associated with neoplasia or infection, although in certain instances lower amounts will be needed because of the increased specificity of the compound. A compound is administered at a dosage that enhances an immune response of a subject, or that reduces the proliferation, survival, or invasiveness of a neoplastic cell as determined by a method known to one skilled in the art. Alternatively, the compound is administered at a dosage that reduces infection by a virus or other pathogen of interest.

The administration of N-803 for the treatment of a neoplasia or an infection may be by any suitable means that results in a concentration of the therapeutic that, combined with other components, is effective in ameliorating, reducing, or stabilizing a neoplasia or infection. N-803 may be contained in any appropriate amount in any suitable carrier substance and is generally present in an amount of 1-95% by weight of the total weight of the composition. The composition may be provided in a dosage form that is suitable for parenteral (e.g., subcutaneously, intravenously, intramuscularly, intravesicularly, intraperitoneally, or other route) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice or nonhuman primates, as a skilled artisan recognizes it is routine in the art to modify the dosage for humans compared to animal models. In certain embodiments it is envisioned that the dosage may vary from between about 0.1 μg compound/kg body weight to about 5000 μg compound/kg body weight; or from about 1 μg/kg body weight to about 4000 μg/kg body weight or from about 10 μg/kg body weight to about 3000 μg/kg body weight. In other embodiments this dose may be about 0.1, 0.3, 0.5, 1, 3, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 μg/kg body weight. In other embodiments, it is envisaged that doses may be in the range of about 0.5 μg compound/kg body weight to about 20 μg compound/kg body weight. In other embodiments the doses may be about 0.5, 1, 3, 6, 10, or 20 mg/kg body weight. Of course, this dosage amount may be adjusted upward or downward, as is routinely done in such treatment protocols, depending on the results of the initial clinical trials and the needs of a particular patient.

In particular embodiments, N-803 are formulated in an excipient suitable for parenteral administration. In particular embodiments, ALT-803 is administered at 0.5 μg/kg—about 15 μg/kg (e.g., 0.5, 1, 3, 5, 10, or 15 μg/kg). For the treatment of bladder cancer, ALT-803 is administered by instillation into the bladder. Methods of instillation are known. See, for example, Lawrencia, et al., Gene Ther 8, 760-8 (2001); Nogawa, et al., J Clin Invest 115, 978-85 (2005); Ng, et al., Methods Enzymol 391, 304-13 2005; Tyagi, et al., J Urol 171, 483-9 (2004); Trevisani, et al., J Pharmacol Exp Ther 309, 1167-73 (2004); Trevisani, et al., Nat Neurosci 5, 546-51 (2002)); (Segal, et al., 1975). (Dyson, et al., 2005). (Batista, et al., 2005; Dyson, et al., 2005). In certain embodiments, it is envisioned that the N-803 dosage for instillation may vary from between about 5 and 1000 μg/dose. In other embodiments the intravesical doses may be about 25, 50, 100, 200, or 400 μg/dose. In other embodiments, N-803 is administered by instillation into the bladder in combination with standard therapies, including mitomycin C or Bacille Calmette-Guerin (BCG).

Pharmaceutical compositions are formulated with appropriate excipients into pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition comprising N-803 may be administered parenterally by injection, infusion, or implantation (subcutaneous, intravenous, intramuscular, intravesicularly, intraperitoneal, intranasally, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions comprising N-803 for parenteral use may be provided in unit dosage forms (e.g., in single-dose ampoules, syringes or bags), or in vials containing several doses and in which a suitable preservative may be added (see below). The compositions comprising N-803 may include one or more lyophilized components including at least one checkpoint inhibitor antibody and/or Bacillus Calmette-Guérin (BCG).

The composition may be in the form of a solution, a suspension, an emulsion, an infusion device, or a delivery device for implantation, or it may be presented as a dry powder to be reconstituted with water or another suitable vehicle before use, such as in the dual chamber device (DCD) as disclosed in the present specification. Apart from the active agent that reduces or ameliorates a neoplasia or infection, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions comprising N-803 may be in a form suitable for sterile injection. To prepare such a composition, the suitable active antineoplastic/anti-infective therapeutic(s) may be dissolved or suspended in a parenterally acceptable liquid vehicle prior to injection, as used in the DCDs disclosed in the present specification. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

The present invention provides methods of treating neoplastic or infectious disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplastic or infectious disease or disorder or symptom thereof. The method includes the step of administering to the mammal a therapeutic amount of an amount of a compound herein sufficient to treat the disease, disorder, or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g., opinion) or objective (e.g., measurable by a test or diagnostic method). The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplastic or infectious disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). N-803 may be used in the treatment of any other disorders in which an increase in an immune response is desired.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia or infection in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Preferably, N-803 is administered in combination with an anti-neoplasia or anti-infectious therapeutic such as an antibody, e.g., a tumor-specific antibody or an immune-checkpoint inhibitor, or possibly with albumin. The antibody and N-803 may be administered simultaneously or sequentially. In some embodiments, the antibody treatment is an established therapy for the disease indication and addition of N-803 treatment to the antibody regimen improves the therapeutic benefit to the patients. Such improvement could be measured as increased responses on a per patient basis or increased responses in the patient population. Combination therapy could also provide improved responses at lower or less frequent doses of antibody resulting in a better tolerated treatment regimen. As indicated, the combined therapy of N-803 and an antibody could provide enhanced clinical activity through various mechanisms, including augmented ADCC, ADCP, and/or NK cell, T-cell, neutrophil or monocytic cell levels or immune responses.

If desired, N-803 is administered in combination with any conventional therapy, including but not limited to, surgery, radiation therapy, chemotherapy, protein-based therapy, or biological therapy. Chemotherapeutic drugs include alkylating agents (e.g., platinum-based drugs, tetrazines, aziridines, nitrosoureas, nitrogen mustards), anti-metabolites (e.g., antifolates, fluoropyrimidines, deoxynucleoside analogues, thiopurines), anti-microtubule agents (e.g., vinca alkaloids, taxanes), topoisomerase inhibitors (e.g., topoisomerase I and II inhibitors), cytotoxic antibiotics (e.g., anthracyclines) and immunomodulatory drugs (e.g., thalidomide and analogs), possibly with albumin.

Pharmaceutical compositions comprising N-803 may be assembled into kits or pharmaceutical systems for use in treating a neoplasia or infection. Kits or pharmaceutical systems according to this aspect of embodiments of the invention disclosed herein may comprise a carrier means, such as a box, carton, tube, having in close confinement therein one or more container means, such as one or more dual chamber devices (DCDs), vials, tubes, ampoules, bottles, syringes, or bags. The kits or pharmaceutical systems of some embodiments the invention may also comprise associated instructions for using N-803.

Embodiments of the present invention may be configured for use with patient-specific therapeutics as discussed above in the Summary, and in further detail below and in U.S. Pat. No. 11,894,109 titled "Production And Delivery Tracking And Sample Verification Of Patient-Specific Therapeutics", which is incorporated herein by reference in its entirety. Such patient-specific therapeutics may also be configured for use with biological sample tracking chains, systems and methods as disclosed in U.S. Pat. No. 10,923,215 titled "Sample Tracking via Sample Tracking Chains, Systems and Methods" which is incorporated herein by reference in its entirety.

FIG. 1A illustrates a block diagram of an exemplary distributed computer system 100 used in embodiments of the present invention. Client node 110 may comprise an end user device such as a smart phone, tablet, or laptop or desktop computer, and be communicatively coupled to a transmitter or chip attached, associated with, or coupled to dual chamber device (DCD) 112 or other multi-chambered device for dispensing medicaments by injection or other means. Upon receiving data from the transmitter or chip associated with DCD 112, or scanning a QR code, bar code, or other unique identifier associated with DCD 112 (e.g., hash value, patient identifier, doctor identifier, RFID, hospital identifier, GUID, UUID, etc.), client node 110 may communicate via network 160 with one or more distributed ledger hosts 178 storing the one or more distributed ledgers (e.g., therapeutic blockchains, notarized ledger, etc.) running on one or more computing nodes 120. In some embodiments the DCD can be instrumented with RFID tags that correspond to one or more state object on notarized ledger 175 of FIG. 1B for tracking purposes. Furthermore, the DCD could be in some embodiments a smart device that transmits its state (e.g., during delivery to the patient facility, the rate of dispensing of the medication, etc. during use, or during shipping, etc. Further DCD smart devices may include one or more communication interfaces (e.g., Bluetooth, 802.11, USB, etc.) through which the device may connect to other devices (e.g., cell phones, tablets, computers, etc.), where such devices may operate as a proxy or hub to a larger network. In other embodiments, the DCD can include global positioning system (GPS) transmitter capabilities to ensure that the location of the DCD is at or near the patient's location down to within a specified distance, for example. In some embodiments, the DCD may be "locked" for use only in specific geo-fenced areas or bound to a location via S2 cell identifiers (see URL s2geometry.io/devguide/s2cell_hierarchy.html) to ensure the device may only be used proximate to the specific patient for which it is intended. For example, the DCD's identifier may be embodied as a non-fungible token (NFT) on the notarized ledger where the NFT represents the state of the DCD from creation through final use. In such cases, the DCD may be locked to one or more specific S2 cells based on the S2 cell identifiers. Thus, the DCD may only be used when the DCD is actually in the S2 cell or cells where the patient is located. One should appreciate that the DCD may also be locked according to a path of S2 cells where the path or set of S2 cells form a logistic chain through which the DCD is allowed to travel from production through use.

In other embodiments, the DCD may be locked for use only by the specific patient for whom the device was intended, and is unlocked by the patient before use via one or more scans of biometric data, including but not limited to iris scans, face scans, fingerprint scans, audio voice scans, or scans of genomic data. Scans of genomic data may be provided using any of a variety of techniques known in the art, including polymerase chain reaction (PCR) technology for providing genomic data. One example of PCR technology that may be used in embodiments of the disclosed invention includes DNA Nudge (see URL www.dnanudge.com/pages/the-science-bit and U.S. Pat. Nos. 10,093,964 and 10,811,140 both of which are incorporated by reference in their entirety), which provides a portable PCR apparatus that operates using a cartridge containing a multiplex array of 72 wells preloaded with well-researched marker strands of DNA. A genetic sample may be obtained from the patient, e.g., by swabbing for a nasal sample or saliva sample and injected into the wells of the cartridge. If the DNA of the patient's sample matches any of the marker strands, of DNA, a chemical reaction takes place activating the microchip in the PCR machine. The portable PCR machine rapidly heats then cools the DNA sample inside the cartridge, repeating the process may times over until the sample is sufficiently large to switch on the microchip, and the DNA results may be sent directly to the patient's smartphone or other user device within 90 minutes, and may be communicated and stored securely in medication tracking environment 100 as described below.

Figure 1B:
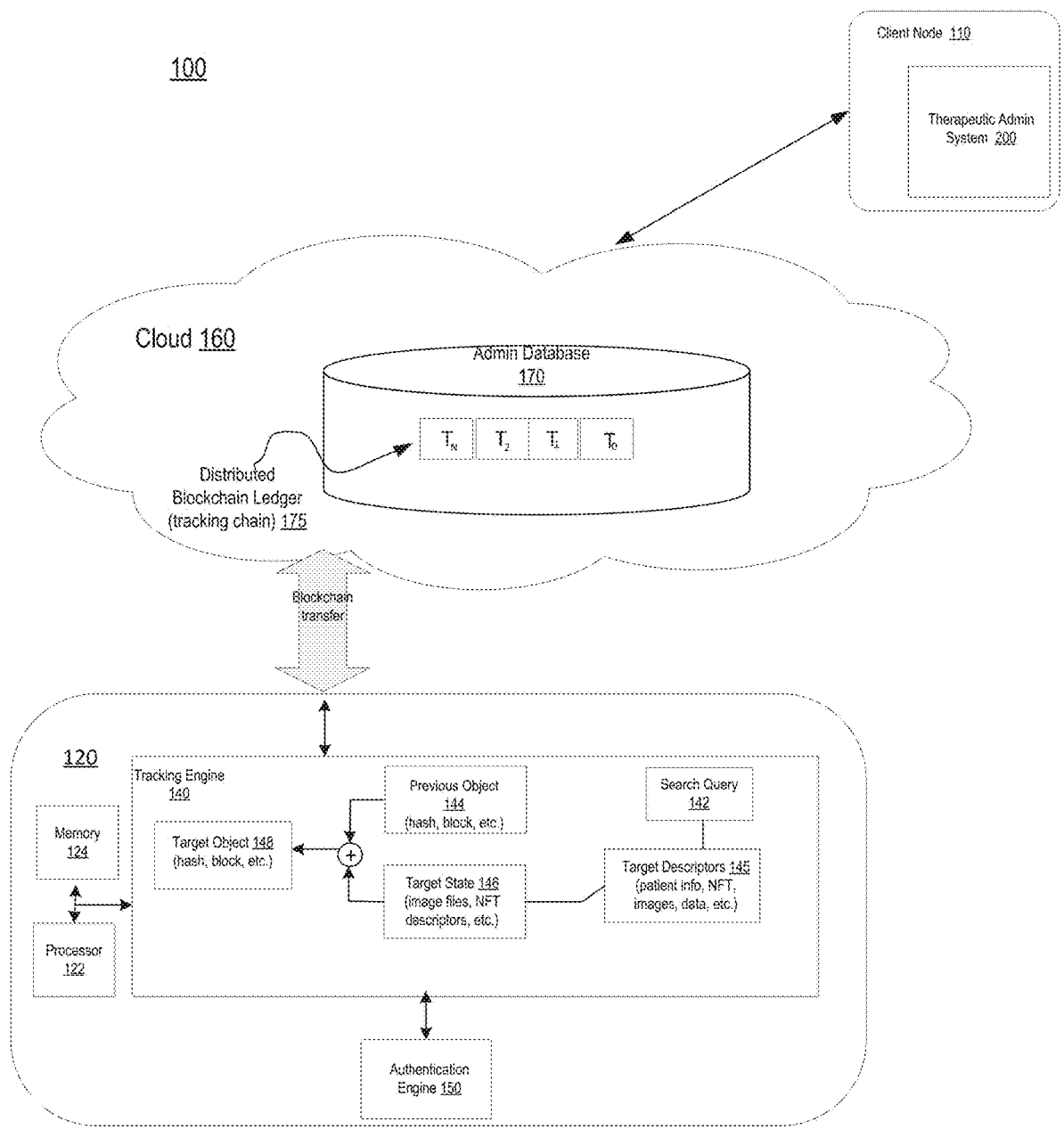
FIG. 1B illustrates a block diagram of a medication tracking environment in accordance with an embodiment of the present disclosure.

FIG. 1B illustrates an embodiment of medication tracking environment 100 where intrinsic or extrinsic properties or features of a medication are used to create medication tracking chain (e.g., notarized ledger) 175. In some embodiments, notarized ledger 175 may comprise a distributed ledger, a blockchain, a hash-graph, a directed acyclic graph, a linked list, or other data structure known in the art that are robust against modification or tampering. Administration database 170 stores one or more of notarized ledger 175 where each notarized ledger 175 may represent a life cycle or possibly an audit trail of a medication or a patient therapeutic from patient diagnosis through production to final administration to the patient, and possibly through final outcome of the therapy. Although one stakeholder (e.g., clinician, physician, manufacturing technician, pharmacist, etc.) may potentially be operating therapeutic administration system 200 running on client node 110 to track patient medications as discussed in relation to some embodiments, it should be appreciated that the medication tracking environment 100 can support multiple users or other stakeholders who wish to interact with one or more of notarized ledger 175. In some embodiments, notarized ledger 175 represents one or more digital data records stored in a computer readable non-transitory memory, possibly protected from tampering or for security reasons by adhereing to a FIPS-140 standard, FIPS-140-2 or FIPS-140-3 for example. Although the process is described with respect to a single tracking chain 175, environment 100 may support tracking of multiple patient-specific medications or therapeutics.

Medication tracking chain 175 represents one or more digital data records stored on a computer readable non-transitory memory. In the example above, medication tracking chain 175 is stored in the memory of administration database 170 as records in a file system, on a hard disk, in solid state memory, or in RAM for example. Administration database 170 is a computing device configured to retrieve data relating to medication tracking chain 175 based on one or more query criteria that can be defined according to the indexing system of database 170. In some embodiments, administration database 170 and/or tracking engine 140 can operate as a medication tracking search engine. Example database technologies that are suitable for use in constructing medication database 170 include MySQL, No SQL, MongoDB, Riak, CouchDB, OpenCog, ArangoDB, or other database technologies, relational or otherwise, known in the art. In some embodiments, medication database 170 could also include a look-up table in memory or even an entire blockchain that comprises medication tracking chain 175. When medication tracking chain 175 is implemented as a blockchain (e.g., possibly operating based on available blockchains software such as Solana, PolyGon, BitCoin, etc.), medication tracking chain 175 may be implemented in some embodiments as a blockchain browser to accept queries. Medication tracking chain 175 or its individual state objects are indexed in some embodiments by the corresponding intrinsic or extrinsic properties of the medication's various states, including but not limited to intrinsic or extrinsic manufacturing properties related to the various states of manufacturing of the therapeutic. Database 170 may further be configured to retrieve data relating to one or more medication tracking chains 175 based on one or more query criteria (e.g., a patient name, a patient image, patient biometric data, patient genomic data, a RF label, a bar code, a hash, a QR identifier, GUID, UUID, etc.) that may be used to identify and return a particular block chain or a block in a notarized ledger.

Medication tracking chain 175 is coupled with tracking engine 140 running on one or more distributed ledger hosts 120 communicatively coupled (as shown through one or more connections 178 in FIG. 1A) as part of therapeutic distributed ledger tracking chain 175 in some embodiments to allow tracking engine 140 to access the one or more medication tracking chains 175. In some embodiments as shown, tracking engine 140 executes on one or more processors 122 running on host 120 and communicatively couples with administration database 170 over network (cloud) 160 (e.g., Internet, intranet, WAN, LAN, WLANB, P2P, wireless, cellular, ad-hoc, etc.). Network 160 can include a wireless network (e.g., WUSB, 802.11, 802.15, 802.16, cellular, etc.), wired network (e.g., Ethernet, circuit switched network, ATM, etc.), or any combination of wireless and wired networks as known to those skilled in the art. Medication tracking engine 140 may comprise a computing device configured to track a medication through an analysis and/or manufacturing process (e.g., generation of a patient-specific therapeutic based on a biological sample of the patient, etc.).

In some embodiments, medication tracking engine 140 comprises a server system, workstation, tablet, cell phone, or other suitable computing device 120 capable of accessing database 170 locally e.g., in the same computer, on the same network) or remotely (e.g., over the Internet, WAN, etc.) via a web or other suitable interface (e.g., HTTP, HTTPS, TCP/IP, UDP/IP, SSL, SSH, FTP, etc.) to access memory 124 and processor 122. In other embodiments, medication tracking engine 140 may operate as a cloud-based infrastructure (e.g., SaaS, IaaS, PaaS, Chain-as-a-Service, Ledger-as-a-Service etc.) possibly based on one or more existing private, hybrid, public, and/or commercially available cloud systems (e.g., Amazon AWS, Microsoft Azure, Google Cloud, etc.). In some embodiments, medication tracking engine 140 comprises a digital notarized ledger management system adapted from ledgers as disclosed in U.S. Pat. No. 11,880,824 to Witchey et al, "Managing Digital Blockchains via Digital Tokens, Systems, Methods and Apparatus", which is incorporated herein by reference in its entirety.

Medication tracking engine 140 tracks, stores, and/or accesses information related to a patient-specific therapeutic 112. Medication tracking engine 140 may leverage current state 146 in order to track processing of the patient specific therapeutic 112. For example, medication tracking engine 140 may access one or more of tracking chains 175 from administration database 170 where distributed ledger 175 is stored or from other memories where the tracking chains may be stored. For example, tracking engine 140 may access the initial block (To) typically referred to as a genesis block for a particular patient-specific medication and may compile one or more pieces of intrinsic or extrinsic manufacturing data pertaining to analysis or processing of the medication to generate current (target) state 146. In some embodiments, target state 146 may include extrinsic manufacturing information (e.g., a technician name, doctor identifier, patient identifier, a date, a location, etc.) and/or intrinsic manufacturing information (e.g., content description, composition data, appearance of the biological sample or therapeutic, information pertaining to the process conditions, additives, etc.). Extrinsic and intrinsic patient data may also be provided, for inclusion of part or all of this information into the current state 146. In addition, tracking chain 175 may also include, in addition to information about the medication content, it may also include information about the rates (or ratios) that each chamber of the dual chamber device (DCD) may deliver their content. In one embodiment, rate of delivery can be associated with administration of a patient-specific therapeutic to the patient. Such information may be stored as a digital data structure, possibly created based on an instantiated object class in memory, where the instantiated object has parameters, attributes, or methods that comprise the extrinsic or intrinsic patient data. In some embodiments, tracking chain 175 may also include one or more pointers to data that may be stored off the notarized ledger (i.e., "off chain"), particularly where the data involves large amounts of data. For example, large amounts of patient data may be stored off chain where the pointers (e.g., URLs, URIs, DOIs (Digital Object Identifiers), HOIs (Healthcare Object Identifier, see U.S. patent U.S. Pat. No. 11,017,897 incorporated by reference in its entirety), addresses, etc.) provide a link to where the data may be obtained.

In some aspects, a user (e.g., a manufacturing technician), may provide manufacturing related data to be included as intrinsic or extrinsic manufacturing data at one or more process steps used to generate a current state 146. In other embodiments, a user may add an additive at one or more points in the manufacturing process (e.g., to later verify sample identity via an assay as provided herein or according to the techniques known in the art), and the additive may be provided as data to generate current state 146. Current state 146 may include other modalities of data including information provided by sensors in the manufacturing process. One should appreciate that DCD data may be linked into the tracking chain in aggregate, or each chamber may have its own data linked into the tracking chain individually.

Medication tracking engine 140 may leverage the compiled information (e.g., intrinsic, or extrinsic manufacturing data, intrinsic or extrinsic patient data, etc.) as search query terms allowing search query (search engine) 142 to access particular tracking chains or a block or record in a tracking chain. Typically, the search query is submitted to administration database 170 to return a particular distributed ledger 175 corresponding to a particular patient-specific therapeutic 112.

In general, medication tracking engine 140 may retrieve at least one previous state object 144 from database 170 based on search query 142. Previous state object 142 is an instantiated data object, which represents at least one previously recorded state of the labeled patient therapeutic. In this example, the labeled therapeutic is illustrated as having three previous states listed as $T_0$, $T_1$, and $T_2$ that represent a state at a previous point in time. Although database 170 returns $T_2$ as previous state object 144, it should be appreciated that database 170 may also return a 'NULL' value indicating that no record yet exists, may return a portion of a matching tracking chain 175, or may return the complete tracking chain 175. Previous state object 144 is not necessarily required to be an immediately preceding state. However, in many embodiments, previous state object 144 is an immediately preceding state relative to the data observed in current target state 146. In some embodiments, $T_0$ may be instantiated as a genesis block for the patient or more specifically for the patient-specific DCD where the genesis block comprises information about the patient, the DCD, the therapy, the doctor, or other data relating to the therapy.

The medication details (e.g., a patient-specific therapeutic), including the DCD, may be represented as one or more digital tokens such as a non-fungible token (NFT), ERC721, ERC 1155, ERC 998, etc. stored in state objects on tracking chain 175 (e.g., blockchain entry associated with a notarized or distributed ledger transaction). For example, each compound may be represented as an NFT. In one embodiment, a digital token can comprise a digital representation of one or more of the following assets: patient data, diagnosis data, vial purchase data, vial filling data, vial shipping data, vial use and disposal data, drug manufacturing data, lyophilization data, reconstitution data, drug administration data, drug storage data, drug shipping data, environmental exposure data (e.g., shock, temperature, etc.,), stability testing data, point of care data, prescription data, or a therapeutic outcome.

Generally speaking, NFT technologies represent single tokens that are unique. Rather than representing the data itself, NFTs typically represent an exchange or transaction related to the data. Thus, NFTs can be considered, in many cases, an indirect representation of the data. Still, the data associated with an NFT may be stored off a record-keeping system to be accessed by the owner of the NFT. NFTs can be created (typically called "minting"), exchanged, burned, or otherwise managed as digital objects, typically via transactions related to the NFTs as recorded on an underlying corresponding digital notarized ledger system. Management of NFTs can be achieved through existing token standards such as via Ethereum smart contract standards. These standards include ERC-721, which defines interfaces by which one may manage NFTs. According to ERC-721, NFT minting, transfers, burning, or other operations are recorded on the Ethereum blockchain to retain a record-keeping system of all desired actions associated with the NFT. ERC-998 defines interface for creating tokens comprising sub-tokens and vice versa. ERC-1155 defines interface by which one can create token sets. As users interact with Ethereum tokens via one or more transactions or operations, the operations are recorded on the Ethereum blockchain thereby forming a record-keeping system of the existence of such tokens in an immutable manner. By using NFTS or other types of record-keeping-system-based tokens as a right-to-access token, private data values can be kept private while also ensuring that other authenticated users are able to retain their rights to access the data as needed. Such uses of NFTs are disclosed further in co-owned U.S. patent application Ser. Nos. 17/590,291 and 18/100,544, the contents of which are incorporated by reference herein in their entireties. NFTs may further be managed using similarity score and other techniques as described in co-owned U.S. patent application Ser. Nos. 17/971,244 and 18/237,829, the contents of which are incorporated by reference herein in their entireties. In some embodiments, NFTs may track location data of the DCD as disclosed in U.S. Pat. No. 11,798,244 to Witchey et al., entitled "Location-Based Digital Token Management Systems, Methods, and Apparatus", the contents of which are incorporated herein by reference in its entirety. For example, a personalized DCD may be represented by an NFT having at least one unique identifier (e.g., an owner address, a token identifier, etc.) that carries information about the DCD, where the information may be stored off ledger. In some embodiments, a unique identifier might represent an owner address of the NFT, say an owner address that is associated with the patient (e.g., patient's ownership address, wallet address, doctor's address, hospital's address, etc.). Such addresses may have two-bit fields. A first bit field might represent the actual owner. A second bit field might represent a state of the DCD from point of conception through use. Each time the DCD changes state, the second bit field may be updated to represent the new state while the first bit field remains constant. Thus, the DCD's NFT may be transferred via a call to the NFT's transfer API from one address to another without changing ownership, but where the transfer to the second address indicates a change in state (see U.S. Pat. No. 11,880,824 referenced above). In a practical sense for some embodiments, a standard 256-bit NFT owner address of the DCD may include a 128-bit field representing a specific patient while the second 128-bit field may represent state. The state bit field could carry any state information, perhaps including: a conception value, a manufacturing value, a therapy value, a shipping value, a geolocation value (e.g., S2 cell identifier, zip code, geo-fence, etc.), a delivery value, an administration value, or other values. In some cases, each bit field may represent a state, in other cases the bit field may simply be integers, pointers, strings, or other digital values. From a use perspective, the DCD's NFT may be minted upon a doctor's ordering of a therapy, then the DCD's life cycle is tracked via the state bit field, and then after administration, the DCD's NFT may be burned by calling the NFT's burn API thereby destroying the NFT, but also creating an immutable audit trail of the DCD. While this example provides for two 128-bit fields for a 256-bit address, any practical number of bit fields are contemplated for various address sizes. Three, four, five, or more bit fields may be useful. For example, a first bit field may represent the owner, a second bit field may represent a time-stamp associated with a state change, a third bit field may represent a location where the state change occurred, a fourth bit field may represent the actual state change, and so on.

Previous state object 144 can be packaged using various techniques. In some embodiments, previous state object 144 can be presented to tracking engine 140 in its native form; e.g., as a binary record, a file, raw text, or other format by which previous state object 144 is stored. In other embodiments, administration database 170 can re-package previous state object 144 into a desired format for delivery to tracking engine 140. Example formats can include a CSV file, a binary object, a BLOB, a serialized data structure (e.g., YAML, XML, JSON, etc.), or other formats. In some aspects, previous state object 144 can include a block token, typically a hash digest, which represents or identifies previous state object 144. In some aspects, a hash digest is a bit string of a fixed size, e.g., about 128 to 256 bits in length, or more. A hash function may be used to map data of an arbitrary size to a fixed size hash digest. If one bit of the arbitrary sized data changes, a different digest will be generated by the hash function. Therefore, hash digests are suitable for tracking data integrity as well as other applications as presented herein. In other aspects, a cryptographic function may be used to generate the hash digest.

Tracking engine 140 also generates or otherwise instantiates one or more of current state 146, which may be an intermediate data structure stored in the memory of medication tracking engine 140 in preparation of creating a current target state object 144. For example, current state 146 may include extrinsic and intrinsic manufacturing data, including digital images, video, audio, sensor, or other forms of data added by a user or obtained or compiled during process steps. In some embodiments, manufacturing data could include details about genetic sequences, active/effective ingredients, time of manufacture, etc. that can be folded into the address and/or identifier of one or more state objects stored on the notarized ledger. For example (one of many examples), N-803 has a specific mutation called N72D, which may be hashed with other information to create a resulting hash value (say SHA256), which can then be used as the identifier of an NFT used to represent the treatment.

With respect to digital images, current state 146 could include one or more descriptors generated according to one or more image processing algorithms. The descriptors could include one or more of the following types of descriptors SIFT, SURF, GLOH, TILT, DAISY, HOG, Canny edges, corners, blob descriptors, textures, shape descriptors, or other types of descriptors. Current target state 146 may also include one or more target descriptors 145, such as intrinsic and/or extrinsic patient and/or biological sample data, including bar code information, RFID codes, sample identifiers, name, time stamps, metadata, location, medication prescription or dispensing information, or other types of information.

Once the data associated with current state 146 has been collected, medication tracking engine 140 instantiates current target state object 144 in memory as a function of current (target) state 146 and previous state object 144. When current (target) state object 148 is instantiated, it may be initially created having NULL values that are then populated after instantiation. Alternatively, current (target) state object 148 can be created having fully fleshed out values by passing data from current target state 146 and previous state object 144 to the constructor method of current target state object 148. In some embodiments, current target state object 148 can also be constructed based on external data, such as a hash digest from one or more external distributed, public ledgers (e.g., BitCoin, LiteCoin, Ethereum, Solana, etc.) as form of notarization. According to certain aspects, external data from a public ledger, such as a hash digest associated with BitCoin, can be used as a notary, providing an independent measure of the validity of the timestamp associated with the sample state object. The public ledger data or hash digest acts as an external timestamp that is independent of the medication tracking chain with respect to a particular point of time or a time thereafter. Thus, generating a current target state object using the public ledger provides an independent validation that the data from the corresponding block has not been tampered with or modified.

In some embodiments, the block of data represented by current target state object 148 depends directly on the previous state of the biological sample/therapeutic. Thus, a blockchain of intrinsic states may be formed, thereby forming an audit trail for the DCD.

Tracking engine 140 links current target state object 146 to previous state object 144 to continue building the medication tracking chain. For example, current target state object 148, labeled here as $T_N$, may include data from current target state 146 as well as a hash digest generated by hashing data from current target state 146 along with a hash digest from the previous state object 144. The linking function used to combine or otherwise link the previous state object 144 with the current state 146 is shown by the "Circle-Plus" symbol. Once current target state object 148 has been instantiated and linked, tracking engine 140 updates distributed ledger (tracking chain) 175 in database 140 with the newly created and linked current target state object 148 (e.g., $T_{N+1}$). Distributed ledger 175 may be updated by tracking engine 140 sending current target state object 148, possibly in a serialized format (e.g., XML, YAML, JSON, etc.), to administration database 140 over network (e.g., cloud) 160. Further, distributed ledger tracking chain 175 and current target state object 480 may be indexed by the newly generated intrinsic and/or extrinsic data.

In general, distributed ledger tracking chain 175 may be instantiated as a single stand-alone tracking chain, possibly a side chain for an existing blockchain or ledger, for a single medication to represent the medication's manufacturing, lyophilization, storage, shipping, point of care, reconstitution, administration, and therapeutic outcome life cycle. Thus, unlike cryptocurrency-based block chain implementations, distributed ledger tracking chain 175 or other notarized ledger may remain self-contained and relatively small without incurring unlimited growth or requiring specialized hardware resources. Further, in some embodiments distributed ledger tracking chain 175 does not require a significant amount of work to create a next block, rather tracking engine 140 can quickly execute the desired linking function without requiring a solution to a time-consuming cryptographic puzzle (e.g., proof of work, a hash digest with a specific signature, etc.) thereby decreasing the time necessary to index or link the DCD data to a notarized data structure.

The distributed ledger tracking chain 175 is updated based on a workflow of processing a biological sample into a therapeutic. A workflow may comprise multiple processing steps, with one or more steps in the workflow altering the physical or molecular characteristics of the medications (e.g., antibodies such as checkpoint inhibitor antibodies) to form the therapeutic. Thus, the distributed ledger tracking chain provides a way in which to track the medication compounds through the entire workflow of producing a corresponding therapeutic, while maintaining a record of physical and/or molecular characteristics at various steps of the workflow. In some approaches, each step of the workflow may be recorded in the distributed ledger tracking chain. In other approaches, a subset of steps of the workflow may be recorded in the sample tracking chain. Thus, these techniques are suitable for managing a population of patient medications, at different processing stages of a workflow, to reduce errors occurring from mix-ups.

Distributed ledger tracking chain 175 and its individual blocks may be indexed using various techniques to provide quick retrieval and/or management using search query engine 142. As distributed ledger tracking chain 175 comprises many states wherein each state has its own associated intrinsic and extrinsic data, the values or metrics derived from these properties can be used to index distributed ledger tracking chain 175 and its corresponding sections. Thus, one or more metrics associated with the physical sample's intrinsic or extrinsic data may be used to retrieve tracking chain 175 or portions (e.g., blocks, etc.) thereof.

The present approach is considered superior to the exclusive use of patient information as the properties of the therapeutic are linked to the contents of the container, which reduces potential errors generated by mishandling or mislabeling of samples. The techniques presented herein are not limited to this example workflow. In general, the techniques presented herein can be used to track any number of patient medications or therapeutics through one or more steps of a manufacturing workflow to generate a therapeutic for a specific patient. For example, companies providing genetic analysis services could utilize the tracking techniques provided herein, to monitor patient therapeutics and/or related biological samples as they are processed (e.g., through various stages of DNA sequencing workflows, RNA sequencing workflows, proteomics analysis workflows, immunoassay workflows, biomarker analysis workflows, purification workflows, or any combination thereof, etc.), to greatly reduce errors arising from manual handling of patient therapeutics. Additionally, if processing errors or discrepancies are discovered at a later point in time (e.g., from mishandling by a particular technician, from contamination introduced by a particular instrument, from using a defective reagent in manufacturing process, etc.), these techniques can be used to precisely identify which therapeutics of a population of therapeutics have been affected, rather than presuming the entire population has been affected.

Other examples include manufacturing workflows, including large- and small-scale pharmaceutical and biologic manufacturing, as well as other types of manufacturing processes, etc. Intrinsic and extrinsic properties of a manufacturing process can be tracked as a function of time including large- and small-scale pharmaceutical and biologic manufacturing processes (e.g., reagents, time of addition of reagents and/or additives, composition of additives, technician, impurities, formation of product, viral or bacterial contamination, formation of side products, etc.).

Distributed ledger tracking chain 175 may include data about the therapeutic and/or any related biological samples itself. For example, data pertaining to genomic or proteomic sequences (e.g., whole genome sequence, whole exome sequences, known mutations, SNP patterns, RNA-seq data, proteomics, etc.), chemical composition, etc. may be associated with blocks of the tracking chain 175. In other aspects, the data pertaining to genomic or proteomic sequences may be included on the container in which the therapeutic is placed (e.g., for sending back to a point of care facility for administration to a patient).

Tracking chain 175 as presented only has four blocks shown representing four states for illustrative purposes and should not be considered limiting. Rather, it should be apparent to the reader that distributed ledger tracking chain 175 can include any arbitrarily large number of blocks and/or corresponding states. Such chains can include thousands, millions, or even more blocks depending on the nature of the chain. While distributed ledger tracking chain 175 is shown as a single, standalone chain, it may compose larger structures having many other features. In some embodiments, tracking chain 175 may comprise one or more side chains, possibly a side chain for each DCD, each patient, each care giver, or other configuration. Thus, tracking chain 175 may comprise a chain of device-specific or even patient-specific side chains. Side chains may be created for each chamber on a DCD in some embodiments. Side chains may also include in some embodiments information about synthetic genomic variants used to authorize transactions as disclosed in commonly owned U.S. Pat. No. 10,050,959, and related commonly owned and granted or co-pending U.S. patent application Ser. No. 18/084,449 (U.S. publication 2023/0262055); Ser. No. 17/707,925 (U.S. Pat. No. 11,785,004); and Ser. No. 16/034,271 (U.S. Pat. No. 11,785,002); all of which are incorporated by reference herein in their entirety. As an example, a patient may use secure transaction devices as disclosed in the above-mentioned patents and patent applications to authorize access to the DCD and unlock the mechanism for dispensing the medication as disclosed herein.

There are numerous techniques available by which distributed ledger tracking chain 175 can be instantiated. In some embodiments, tracking chain 175 comprises a set of data blocks linked by recursive hash digests, possibly along with pointers or links. Each block could be stored as a separate record in a database. Other embodiments provide for instantiation of distributed ledger tracking chain 175 as a true blockchain, wherein the blockchain may be part of a private ledger. Existing technologies may be adapted for use to create tracking chain 175, such as BitCoin, Ethereum (see URL www.ethereum.org), ZCash, or the Hyper Ledger Project (see URL www.hyperledger.org), etc.

In view that the blocks of the blockchain can include patient data, the data can be secured via one or more cryptographic techniques (e.g., 3DES, AES, ECC, homomorphic encryption, etc.). For example, the private data stored in the blocks of distributed ledger tracking chain 175 can be encrypted based on a private key.

In some embodiments, distributed ledger tracking chain 175 may be stored within a graph database. For example, each state or block in tracking chain 175 may be stored as a node within the graph database schema wherein the transition from one state to another represents the edge between the nodes. Further, extrinsic and/or intrinsic information can be stored as properties for the nodes and/or edges. Thus, the graph database can be used to retrieve quickly relevant information not just about individual tracking chains 175, but also relevant information from collections of tracking chains 175 having similar graphs with similar properties. Such an approach is advantageous when storing or analyzing large numbers of manufacturing processes. Example graph database implementations that may be leveraged to store one or more tracking chains 175 include Neo4j, OpenCog, and ArangoDB, among others. In some embodiments, graph databases such as OpenCog, which provides an AI framework, might be more desirable when tracking chains 175 are coupled to treatments and outcomes of patients. Such a coupling provides a solid foundation for generating automated, reasoned hypotheses about a new patient's possible outcomes based on comparison of the patient's tracking chain 175 to previous, known medication tracking chains and outcomes. Example reasoning engines that can be adapted to leverage graph database implementations of tracking chains 175 are described in co-owned U.S. Pat. No. 9,262,719 to Soon-Shiong titled "Reasoning Engines", filed internationally on Mar. 22, 2012.

One should appreciate that distributed ledger tracking chain 175 also provides a solid foundation for compliance with one or more regulations. For example, distributed ledger tracking chain 175 may include block-level data that complies with IEC 62304 audit trail requirements, 21 CFR part 11 requirements, HIPAA regulations, Health Level 7 (HL7) support, or other features. Further, the memory storing tracking chain 175 may be configured to comply with one or more security standards, possibly including FIPS 140-2.

In general, the methods and techniques provided herein may in some embodiments additionally cover tracking any suitable type of biological sample that may be used in conjunction with or in manufacturing medications tracked using distributed ledger tracking chain 175, including but not limited to saliva, urine, blood, ovum, sperm, stool, skin, sweat, hair, etc.

Figure 2:
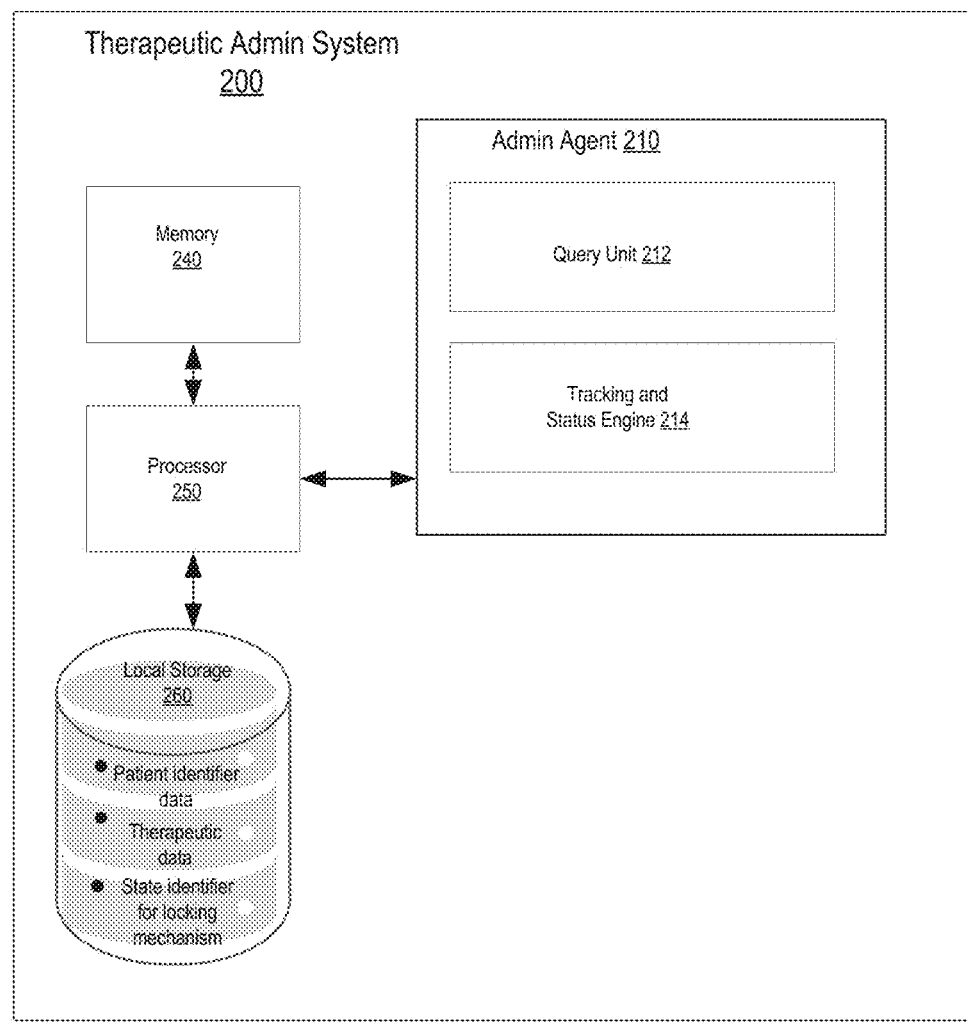
FIG. 2 illustrates a block diagram of an exemplary therapeutic administration system according to an embodiment of the present disclosure.

FIG. 2 illustrates a block diagram of an exemplary therapeutic administration system 200 according to an embodiment of the present invention. In some embodiments, therapeutic administration system 200 runs on client node 110, and comprises one or more processors 250 and memory 240. Administration agent 210 executes on processor 250, and receives an administration request comprising a patient identifier, which may be obtained from scanning a labeled DCD or receiving transmitted data from an RFID device or other transmitter located on the DCD. Query unit 212 queries administration database 170 and retrieves one or more notarized ledgers (e.g., blockchains) corresponding to the patient identifier. Tracking and status engine 214 will receive the notarized ledger and retrieve information from the notarized ledger into local storage 250 including the patient identifier, a digital token corresponding to an owner (e.g., an authorized user of the DCD), and therapeutic data including information on, e.g., one or more lyophilized components within one or more vials of the DCD, and rate and/or dispensing instructions for dispensing the lyophilized components and/or reconstitution buffer contents of the DCD, which may also include state identifier information for the DCD locking mechanism to control the opening of the chambers of the DCD and or a rate of flow or entry from one chamber of the DCD to another chamber of the DCD. Tracking and status engine 214 will also communicate with authentication engine 120 on the one or more notarized ledger hosts 178 to authenticate the digital token, transmit the information needed to create a new notarized ledger transaction (e.g., state object or block), and receive authorization to access the one or more vials of the DCD to unlock and/or control a rate of flow or dispensing of the one or more vials. Techniques for authentication and/or validation of digital tokens used in some embodiments of the disclosed invention are discussed in co-owned U.S. Pat. Nos. 10,885,173; 11,048,788; 11,210,383; 11,455,385; and U.S. Pat. No. 11,899,768. Each of these U.S. patents are incorporated by reference herein in its entirety.

Figure 3A:
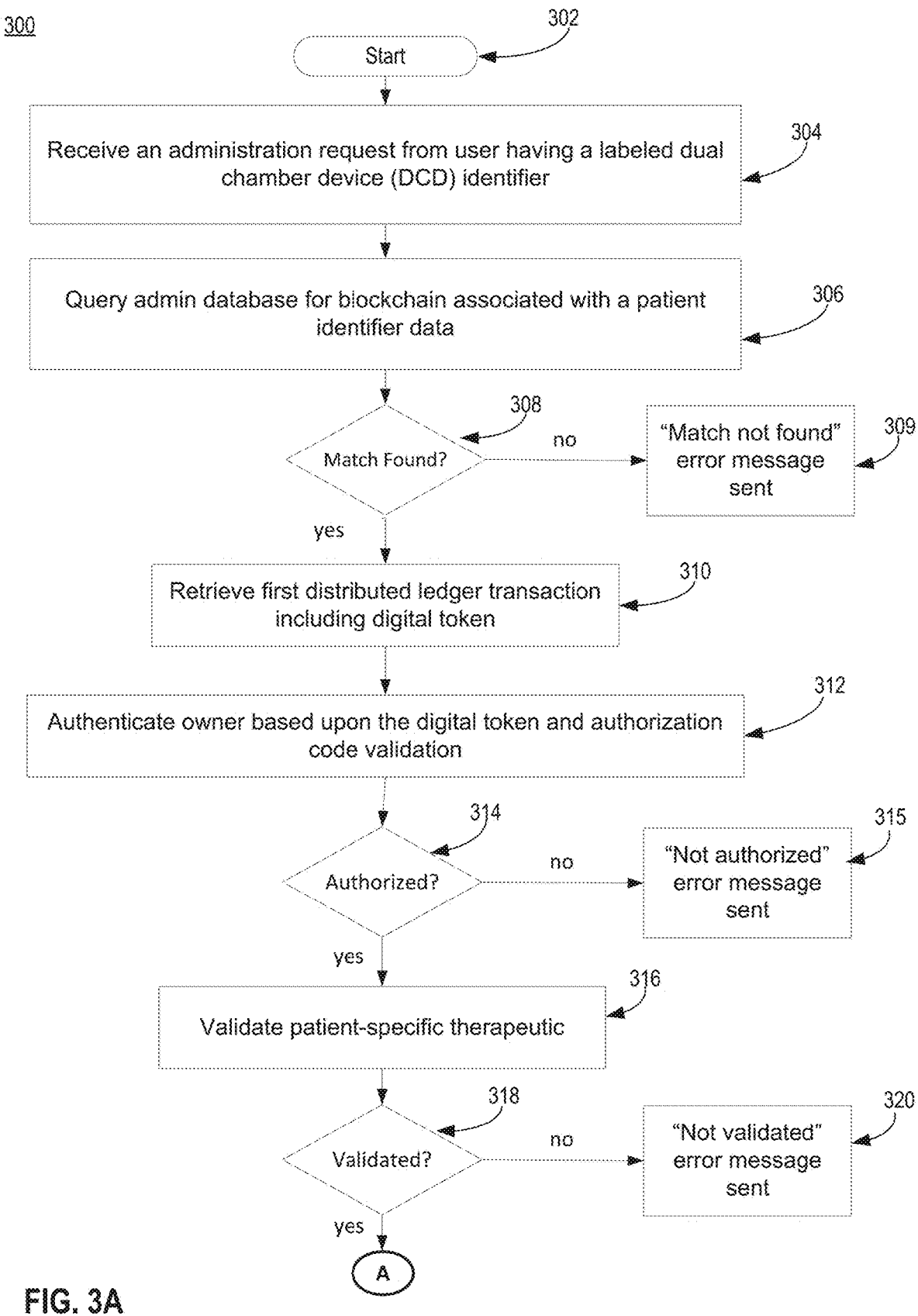
FIGS. 3A and 3B illustrate two flowcharts depicting a computer-assisted method for autonomously tracking and administering medicaments according to an embodiment of the present invention.
Figure 3B:
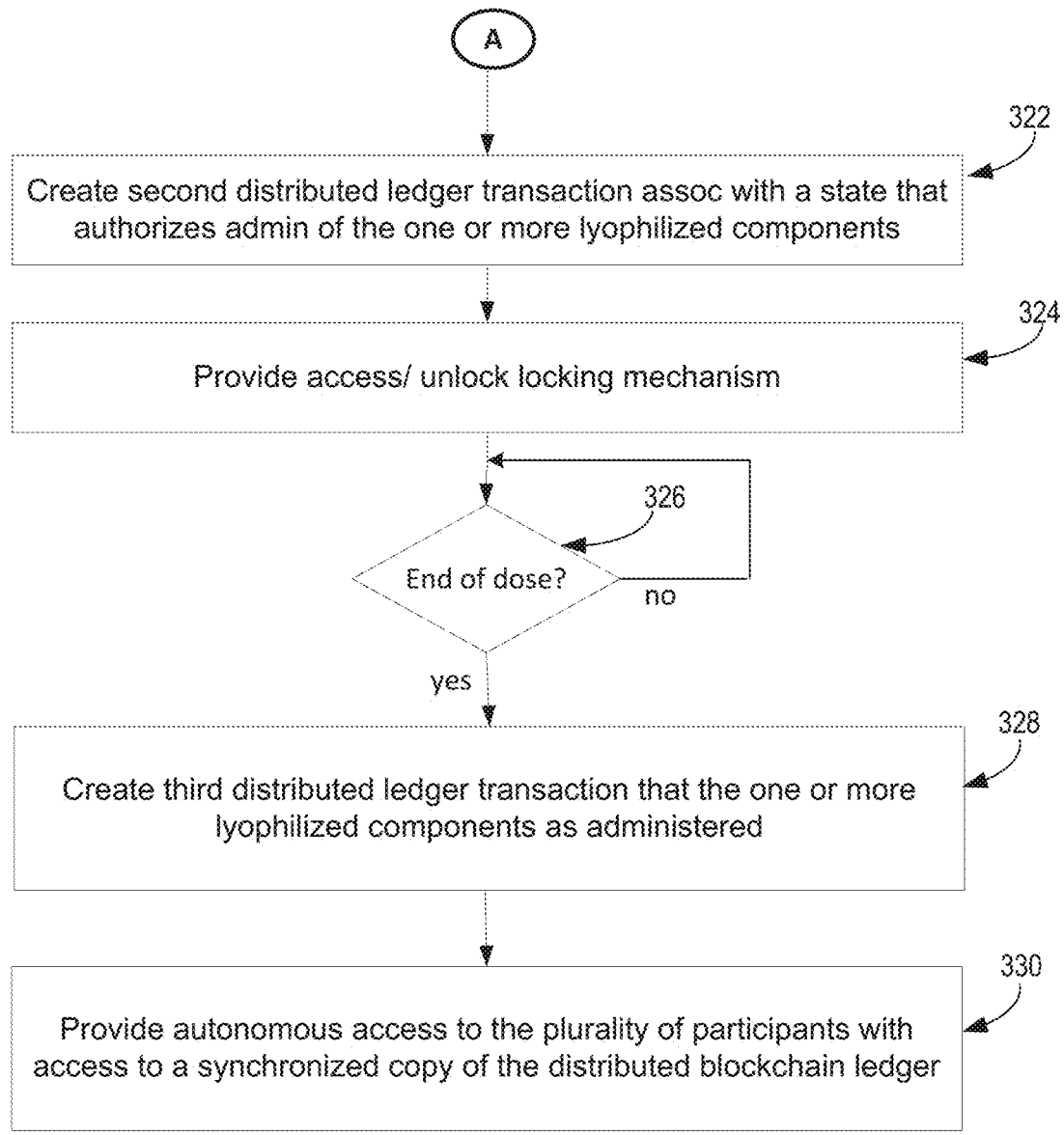

FIGS. 3A and 3B illustrate two flowcharts 300 depicting a computer-assisted method for autonomously tracking and administering medicaments according to an embodiment of the present invention. After start operation 302 on FIG. 3A, therapeutic administration system 200 receives a request from a user having a labeled dual chamber device (DCD) identifier from DCD 112 at operation 304. At operation 306, query unit 212 queries administrative database 170 through cloud 160 to retrieve a notarized ledger (e.g., distributed ledger, blockchain, hashgraph, etc.) associated with a patient identifier data. If a match is found for the patient identifier data at operation 308, a first notarized ledger transaction including a digital token is retrieved at operation 310. If a match is not found for the patient identifier data at operation 308, an error message of "match not found" may be returned to the user at operation 309 via an error message displayed on user device 110 which is running therapeutic administration system 200.

At operation 312, an owner or user is authenticated based upon the digital token, and in some embodiments, one or more authorization code validations may also be used. In one embodiment, a first authorization code is sent to a user device 110 associated with the owner of the labeled DCD based on the digital token, and then a second authorization code may be received from the user in response to sending the first authorization code. If a match is detected between the first authorization code and the second authorization code, the owner or user of the labeled DCD is authenticated based on the detected match.

If the user passes the authentication and authorization operation at operation 314, the patient-specific therapeutic is validated at operation 316. If the owner or user of the patient-specific therapeutic is not authorized, a "not authorized" error message is returned to the user at operation 315 via an error message displayed on user device 110 which is running therapeutic administration system 200 when the user is not authenticated or authorized to access the patient specific therapeutic on DCD 112.

Validation of the patient-specific therapeutic at operation 316 may involve in some embodiments verifying information on the distributed ledger transactions to ensure that the patient-specific therapeutic is the proper prescription administered for the identified patient. If the patient-specific therapeutic is not validated at operation 318, a "not validated" error message is sent at operation 320, and the disclosed method terminates. Once the patient-specific therapeutic is validated at operation 318, the disclosed system and methods will proceed to the operations illustrated in FIG. 3B.

At operation 322, a second notarized ledger transaction is created and associated with a state object that authorizes administration of the one or more lyophilized components. At operation 324, access to a locking mechanism is provided to unlock on or more vials collectively or individually on the DCD to begin the administration of the one or more lyophilized components. In some embodiments, receiving the administration request will trigger therapeutic administration system 200 to facilitate display of a selectable option for unlocking the labeled DCD on an administration agent of a user device 110. System 200 may also be configured to receive an indication of a selection of the option, wherein the selection of the option is made via a user input. Based on the indication, system 200 may in some embodiments access a memory of the user device to retrieve the identifier associated with the labeled DCD.

When an end of dose is reached at operation 326, a third notarized ledger transaction is created at operation 328 which indicates that the one or more lyophilized components have been administered to the patient. Then, at operation 330, autonomous access is provided to a plurality of users or participants to a synchronized copy of the notarized ledger (e.g., blockchain, distributed ledger, hashgraph, etc.).

Figure 4:
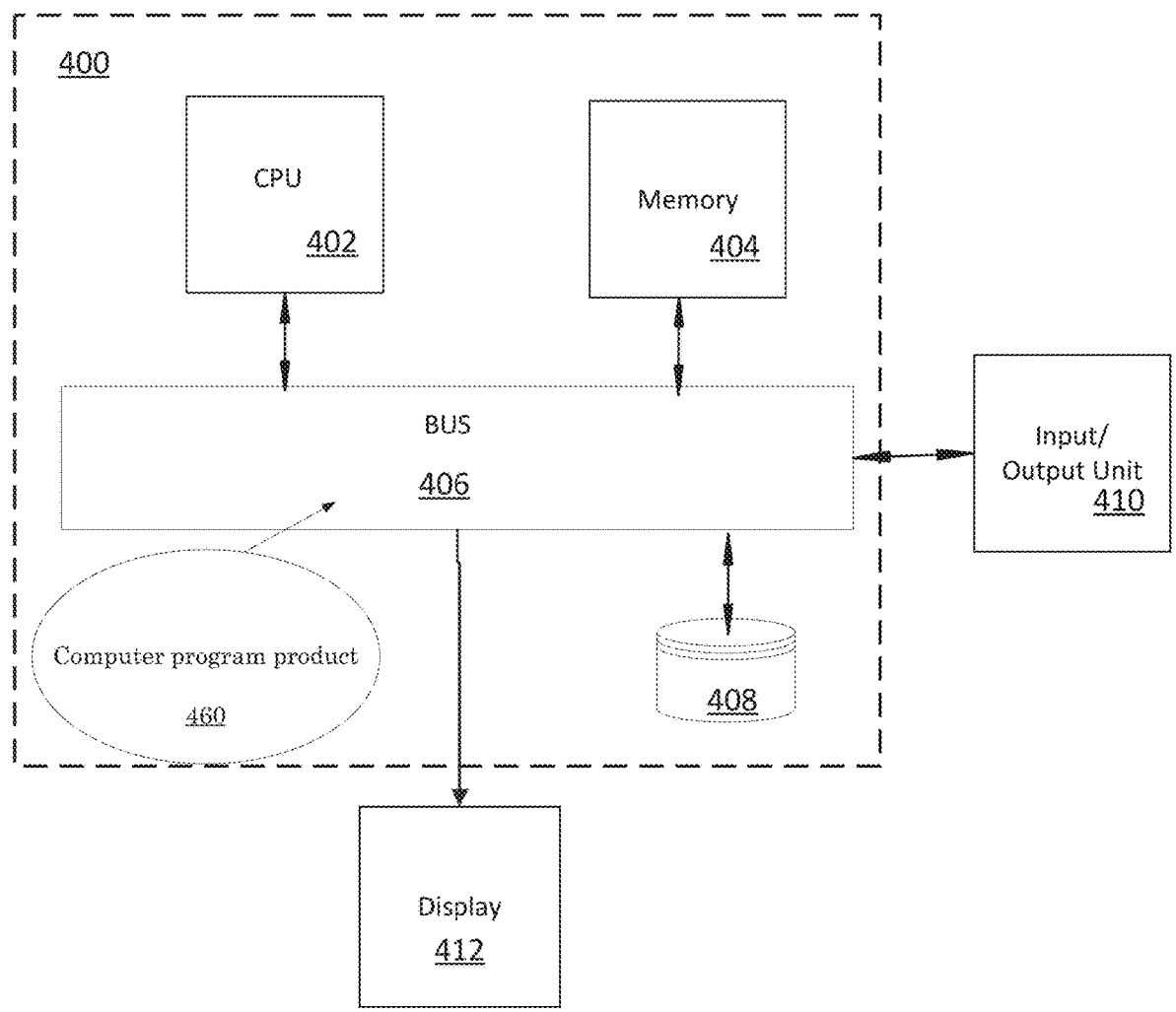
FIG. 4 shows an example of a computer system, one or more of which may be used to implement one or more of the apparatuses, systems, and methods illustrated herein.

FIG. 4 shows an example of a computer system 400, one or more of which may be used to implement one or more of the apparatuses, systems, and methods illustrated herein, such as tracking engine 140, therapeutic administration system 200, and methods 300. Computer system 400 executes instruction code contained in a computer program product 460. Computer program product 460 comprises executable code in an electronically readable medium that may instruct one or more computers such as computer system 400 to perform processing that accomplishes the exemplary method steps performed by the embodiments referenced herein.

The electronically readable medium may be any non-transitory medium that stores information electronically and may be accessed locally or remotely, for example via a network connection. In alternative embodiments, the medium may be transitory. The medium may include a plurality of geographically dispersed media each configured to store different parts of the executable code at different locations and/or at different times. The executable instruction code in an electronically readable medium directs the illustrated computer system 400 to carry out various exemplary tasks described herein. The executable code for directing the carrying out of tasks described herein would be typically realized in software. However, it will be appreciated by those skilled in the art, that computers or other electronic devices might utilize code realized in hardware to perform many or all the identified tasks without departing from the present invention. Those skilled in the art will understand that many variations on executable code may be found that implement exemplary methods within the spirit and the scope of the present invention.

The code or a copy of the code contained in computer program product 460 may reside in one or more storage persistent media (not separately shown) communicatively coupled to system 400 for loading and storage in persistent storage device 408 and/or memory 408 for execution by processor 408. Computer system 400 also includes I/O subsystem 410 and display 412. I/O subsystem 410, processor 402, memory 404, and persistent storage device 408 are coupled via bus 406. Like persistent storage device 408 and any other persistent storage that might contain computer program product 460, memory 404 is a non-transitory media (even if implemented as a typical volatile computer memory device). Moreover, those skilled in the art will appreciate that in addition to storing computer program product 460 for carrying out processing described herein, memory 404 and/or persistent storage device 408 may be configured to store the various data elements referenced and illustrated herein.

Those skilled in the art will appreciate computer system 400 illustrates just one example of a system in which a computer program product in accordance with an embodiment of the present invention may be implemented. To cite but one example of an alternative embodiment, execution of instructions contained in a computer program product in accordance with an embodiment of the present invention may be distributed over multiple computers, such as, for example, over the computers of a distributed computing network.

Instructions for implementing a machine assisted method for administering medicaments implementing any of the above in accordance with disclosed embodiments may reside in computer program product 460. When processor 402 is executing the instructions of computer program product 460, the instructions, or a portion thereof, are typically loaded into working memory 404 from which the instructions are readily accessed by processor 402.

In one embodiment, processor 402 in fact comprises multiple processors which may comprise additional working memories (additional processors and memories not individually illustrated) including one or more graphics processing units (GPUs) comprising at least thousands of arithmetic logic units supporting parallel computations on a large scale. GPUs are often utilized in blockchain applications because they can perform the relevant processing tasks more efficiently than can typical general-purpose processors (CPUs). Other embodiments comprise one or more specialized processing units comprising systolic arrays and/or other hardware arrangements that support efficient parallel processing. In some embodiments, such specialized hardware works in conjunction with a CPU and/or GPU to carry out the various processing described herein. In some embodiments, such specialized hardware comprises application specific integrated circuits and the like (which may refer to a portion of an integrated circuit that is application-specific), field programmable gate arrays and the like, or combinations thereof. In some embodiments, however, a processor such as processor 402 may be implemented as one or more general purpose processors (preferably having multiple cores) without necessarily departing from the spirit and scope of the present invention.

In some embodiments, the notarized ledger can be a standalone data structure, e.g., and individual data structure. In other embodiments, the notarized ledger can be part of a larger blockchain infrastructure, e.g., as part of a hyper ledger or other blockchain based infrastructures or integrated into other notarized ledgers or blockchains. In other embodiments, the notarized ledger may be part of a larger blockchain infrastructure, e.g., associated with a technician or a facility, etc. Examples of storing healthcare data in a large blockchain to create a healthcare historical blockchain (HHBC) may be found in U.S. Pat. Nos. 10,340,038 and 11,386,985 which are each incorporated herein by reference in its entirety.

The techniques disclosed herein may also be utilized as an Operating as a Service (OaaS) using an Application Programming Interface (API). Various analytics can be performed on the notarized ledgers, which in some embodiments comprise linked lists of hash digests. Provided that the various notarized ledgers are stored on a suitable infrastructure, hospitals, scientists, companies, manufacturing facilities, or other entities desiring access to data in one or more distributed ledger transactions (e.g., state objects) may subscribe to a service to access relevant data. Additionally, the techniques presented herein may be used to store and keep some aspects of data private. For example, by including pointers to imaging slides, a $3^{rd}$ party could be provided with access to the slides, and not confidential patient information associated with the slides.

For example, to review all of the microdissections available for a particular type of lung cancer, or associated with a particular clinical study, one could review the notarized ledger to identify relevant samples (e.g., only lung microdissection sites). In other examples, notarized ledgers may be reviewed to establish patient therapeutics or patient biological sample data analyzed by a particular technician or at a particular facility.

To facilitate identification of relevant data, the notarized ledger can include metadata. Various types of metadata can be collected and incorporated into the state object or notarized ledger transaction object to describe the characteristics of, e.g., the patient therapeutic or any biological samples associated with the patient therapeutic., e.g., biological sample thickness, type of cancer, clinical trial information, etc. The notarized ledger can be used to store various types of metadata used to characterize the patient therapeutic, the lyophilized components, the reconstitution buffer, etc. and/or facilitate identification of data of interest, e.g., as part of an OaaS service.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claim, all terms should be interpreted in the broadest possible manner consistent with the context. In particular, the terms "comprise" and "comprising" should be interpreted as referring to elements, compounds, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C, . . . and N, the text should be interpreted as requiring only one element from the group, not A plus N, or B plus N, etc.

While the invention has been particularly described with respect to the illustrated embodiments, it will be appreciated that various alterations, modification, and adaptations may be made based on the present disclosure and are intended to be within the scope of the invention. While the invention has been described in connection with what are presently considered to be the most practical and preferred embodiments, it is to be understood that the invention is not limited to the disclosed embodiments but only by the following claims.

What is claimed is:

1. A computer-assisted method for autonomously tracking and administering medicaments by a tracking system, the method comprising:
   receiving, from a processor of a user device, a request for administering a medicament to a patient, the request comprising a scanned identifier associated with the patient and a labeled dual chamber device (DCD), wherein the labeled DCD comprises a first chamber having one or more lyophilized components, a second chamber having a reconstitution buffer therein, and a locking mechanism comprising a transmitter communicatively coupled to the processor of the user device for controlling access to at least one of the first chamber and the second chamber;
   querying, by a tracking engine comprising at least one processor executing one or more computer readable instructions, an administration database based on the scanned identifier to find a notarized ledger associated with the labeled DCD wherein the notarized ledger comprises at least one notarized ledger entry and is stored in the administration database;

retrieving, by the tracking engine when the notarized ledger is found, a notarized ledger entry comprising a first distributed ledger transaction identifying: i) the one or more lyophilized components within one or more vials of the labeled DCD, ii) a patient-specific therapeutic, and iii) a digital token associated with an owner of the labeled DCD;

receiving from an authentication engine comprising at least one processor executing one or more computer readable instructions, at least one authorization code associated with the owner of the labeled DCD for authenticating the owner of the labeled DCD by at least one authentication technique using the digital token;

validating the patient-specific therapeutic at the authentication engine by verifying the patient as the owner of the labeled DCD by transmitting the at least one authorization code to the user device and receiving the at least one authorization code from the user device identifying the owner of the labeled DCD;

creating, by the tracking engine in response to the validation of the patient-specific therapeutic, a second distributed ledger transaction based on the first distributed ledger transaction and including an indicator identifying the one or more lyophilized components as being authorized for administration to the patient;

authorizing, by the tracking engine in response to the creation of the second distributed ledger transaction, autonomous access to the one or more lyophilized components in the labeled DCD by transmitting the indicator to the user device; and transitioning, by the user device in response to receiving the indicator, the locking mechanism from a locked state to an unlocked state with respect to at least one of the first chamber and the second chamber such that the patient-specific therapeutic can be administered to the patient.

2. The computer-assisted method of claim 1, further comprising:

detecting, by the tracking engine, an end-of-dose indication that the patient-specific therapeutic has been administered to the patient using the labeled DCD; and creating, by the tracking engine in response to detecting the end-of-dose indication, a third distributed ledger transaction based on the second distributed ledger transaction and including an indicator identifying the one or more lyophilized components as being administered to the patient.

3. The computer-assisted method of claim 1, wherein receiving the administration request further comprises:

facilitating display of a selectable option for unlocking the labeled DCD on an administration agent of a user device;

receiving an indication of a selection of the option, wherein the selection of the option is made via a user input; and based on the indication, accessing a memory of the user device to retrieve the identifier associated with the labeled DCD.

4. The computer-assisted method of claim 1, wherein authenticating the owner comprises:

sending a first authorization code to a user device associated with the owner of the labeled DCD based on the digital token;

receiving a second authorization code in response to sending the first authorization code; and detecting a match between the first authorization code and the second authorization code, wherein the owner of the labeled DCD is authenticated based at least on the match detected.

5. The computer-assisted method of claim 1, wherein the first distributed ledger transaction further identifies one or more parameters associated with one or more ratios for the one or more lyophilized components.

6. The computer-assisted method of claim 5, wherein validating the patient-specific therapeutic further comprises:

obtaining a scanned extrinsic label identifier from the labeled DCD;

verifying the scanned extrinsic label identifier according to one or more similarity measures between one or more digital assets associated with the digital token and a therapeutic hash digest; and verifying the one or more parameters associated with the one or more ratios for the one or more lyophilized components according to the one or more similarity measures.

7. The computer-assisted method of claim 1, wherein authorizing autonomous access to the one or more lyophilized components further comprises controlling at least one rate of delivery with respect to at least one of the first chamber and the second chamber wherein the at least one rate of delivery is associated with one or more ratios.

8. The computer-assisted method of claim 7, wherein the at least one rate of delivery is associated with administration of the patient-specific therapeutic to the patient.

9. The computer-assisted method of claim 1, wherein the digital token comprises a digital representation of one or more of the following assets: patient data, diagnosis data, drug manufacturing data, lyophilization data, drug reconstitution data, drug administration data, a drug storage date, a drug shipping date, a point of care, a prescription, or a therapeutic outcome.

10. The computer-assisted method of claim 1, wherein the one or more lyophilized components comprise N-803 and at least one checkpoint inhibitor antibody.

11. The computer-assisted method of claim 1, wherein the one or more lyophilized components comprise N-803 and Bacillus Calmette-Guérin (BCG).

12. The computer-assisted method of claim 1, wherein the labeled DCD comprises multiple interchangeable vials, and wherein the labeled DCD is configured for one or more capsules to be loaded onto a syringe of the labeled DCD in tandem with the vials.

13. The computer-assisted method of claim 1, wherein the notarized ledger comprises one of: a distributed ledger, a blockchain, a hash-graph, or a directed acyclic graph.

14. A medicaments administration tracking system for tracking a patient-specific therapeutic comprising:

an administration database storing one or more therapeutic tracking notarized ledgers, each therapeutic tracking notarized ledger representing digital life cycle data of a patient-specific therapeutic; and at least one processor coupled to the administration database and configured to:

receive, from a processor of a user device, an administration request for administrating a medicament to a patient comprising a scanned identifier associated with the patient and a labeled dual chamber device (DCD), the labeled DCD comprising a first chamber including one or more lyophilized components, a second chamber having a reconstitution buffer therein, and a locking mechanism comprising a transmitter communicatively coupled to the processor of the user device for controlling access to at least one of the first chamber and the second chamber;

query, by a tracking engine comprising at least one processor executing one or more computer readable instructions, the administration database based on the scanned identifier to find a notarized ledger associated with the labeled DCD wherein the notarized ledger comprises at least one notarized ledger entry and is stored in the administration database;

retrieve, by the tracking engine when the notarized ledger is found, a notarized ledger entry comprising a first distributed ledger transaction identifying: i) one or more lyophilized components within one or more vials of the labeled DCD, ii) a patient-specific therapeutic, and iii) a digital token associated with an owner of the labeled DCD;

receiving from an authentication engine comprising at least one processor executing one or more computer readable instructions, at least one authorization code associated with the owner of the labeled DCD for authenticating the owner of the labeled DCD by at least one authentication technique using the digital token;

validate the patient-specific therapeutic by verifying the patient as the owner of the labeled DCD by transmitting the at least one authorization code to the user device and receiving the at least one authorization code from the user device identifying the owner of the labeled DCD;

create, by the tracking engine in response to validation of the patient-specific therapeutic, a second distributed ledger transaction based on the first distributed ledger transaction including the status indicator to a second state identifying the one or more lyophilized components as being authorized for authorized for administration to the patient;

authorize, by the tracking engine in response to the creation of the second distributed ledger transaction, autonomous access to the one or more lyophilized components by transmitting the status indicator to the user device;

transition, by the user device in response to receiving the status indicator, transitions the locking mechanism from a locked state to an unlocked state with respect to at least one of the first chamber and the second chamber such that the patient-specific therapeutic can be administered to the patient;

detect, by the tracking engine, an end-of-dose indication received from the user device that the patient-specific therapeutic has been administered to the patient using the labeled DCD wherein the locking mechanism transmits the end-of-dose indication to the user device; and create, by the tracking engine in response to detecting the end-of-dose indication, a third distributed ledger transaction based on the second distributed ledger transaction including an indicator identifying the one or more lyophilized components as being administered to the patient.

15. The system of claim 14, wherein receiving the administration request comprises the at least one processor being further configured to:

display a selectable option for unlocking the labeled DCD on an administration agent of the user device;

receive an indication of a selection of the option, wherein the selection of the option is made via a user input; and based on the indication, access a memory of the user device to retrieve an identifier associated with the labeled DCD.

16. The system of claim 14, wherein authenticating the owner comprises the at least one processor being further configured to:

send a first authorization code to the user device associated with the owner of the labeled DCD based on the digital token;

receive a second authorization code in response to sending the first authorization code; and detect a match between the first authorization code and the second authorization code, wherein the owner of the labeled DCD is authenticated based at least on the match detected.

17. The system of claim 14, wherein the notarized ledger comprises one of: a distributed ledger, a blockchain, a hash-graph, or a directed acyclic graph.

18. The system of claim 14, wherein the first distributed ledger transaction further identifies one or more parameters associated with one or more ratios for the one or more lyophilized components.

19. The system of claim 18, wherein validating the patient-specific therapeutic comprises the at least one processor being further configured to:

obtain a scanned extrinsic label identifier from the labeled DCD;

verify the scanned extrinsic label identifier according to one or more similarity measures between one or more digital assets associated with the digital token and a therapeutic hash digest; and verify the one or more parameters associated with the one or more ratios for the one or more lyophilized components according to the one or more similarity measures.

20. The system of claim 14, wherein authorizing autonomous access to the one or more lyophilized components further comprises controlling at least one rate of delivery with respect to at least one of the first chamber and the second chamber wherein the at least one rate of delivery is associated with one or more ratios.

21. The system of claim 20, wherein the at least one rate of delivery is associated with administration of the patient-specific therapeutic to the patient.

22. A non-transitory computer-readable medium including computer-readable code for autonomously tracking and administering medicaments, which, when executed by one or more processors, causes the one or more processors to:

receive, from a processor of a user device, a request for administering a medicament to a patient, the request comprising a scanned identifier associated with the patient and a labeled dual chamber device (DCD), wherein the labeled DCD comprises a first chamber having one or more lyophilized components therein, a second chamber having a reconstitution buffer therein, and a locking mechanism comprising a transmitter communicatively coupled to the processor of the user device for controlling access to at least one of the first chamber and the second chamber;

query, by a tracking engine comprising at least one processor executing one or more computer readable instructions, an administration database based on the scanned identifier to find a notarized ledger associated with the labeled DCD wherein the notarized ledger comprises at least one notarized ledger entry and is stored in the administration database;

retrieve, by the tracking engine when the notarized ledger is found, a notarized ledger entry comprising a first distributed ledger transaction identifying: i) the one or more lyophilized components within one or more vials of the labeled DCD, ii) a patient-specific therapeutic, and iii) a digital token associated with an owner of the labeled DCD;

receive from an authentication engine comprising at least one processor executing one or more computer readable instructions, at least one authorization code associated with the owner of the labeled DCD for authenticating the owner of the labeled DCD by at least one authentication technique using the digital token;

validate the patient-specific therapeutic by verifying the patient as the owner of the labeled DCD by transmitting the at least one authorization code to the user device and receiving the at least one authorization code from the user device identifying the owner of the labeled DCD;

create, by the tracking engine in response to the validation of the patient-specific therapeutic, a second distributed ledger transaction based on the first distributed ledger transaction and including a status indicator identifying the one or more lyophilized components as being authorized for administration to the patient; and authorize, by the tracking engine in response to the creation of the second distributed ledger transaction, autonomous access to the one or more lyophilized components by transmitting the status indicator to the user device;

transition, by the user device in response to receiving the status indicator, transitions the locking mechanism associated with the DCD from a locked state to an unlocked state;

detect, by the tracking engine, an end-of-dose indication received from the user device that the patient-specific therapeutic has been administered to the patient using the labeled DCD wherein the locking mechanism transmits the end-of-dose indication to the user device; and create, by the tracking engine in response detecting the end-of-dose indication, a third distributed ledger transaction based on the second distributed ledger transaction that changes the status indicator to a third state identifying the one or more lyophilized components as administered.

23. The computer-readable medium of claim 22, wherein receiving the administration request further comprises causing the one or more processors to:

facilitate display of a selectable option for unlocking the labeled DCD on an administrative agent of the user device;

receive an indication of a selection of the option, wherein the selection of the option is made via a user input; and based on the indication, accessing a memory of the user device to retrieve the identifier associated with the labeled DCD.

24. The computer-readable medium of claim 22, wherein authenticating the owner further comprises causing the one or more processors to:

send a first authorization code to a user device associated with the owner of the labeled DCD based on the digital token;

receive a second authorization code in response to sending the first authorization code; and detect a match between the first authorization code and the second authorization code, wherein the owner of the labeled DCD is authenticated based on at least the match detected.

25. The computer-readable medium of claim 22, wherein the notarized ledger comprises one of: a distributed ledger, a blockchain, a hash-graph, or a directed acyclic graph.

26. The computer-readable medium of claim 22, wherein the first distributed ledger transaction further identifies one or more parameters associated with one or more ratios for the one or more lyophilized components.

27. The computer-readable medium of claim 26, wherein validating the patient-specific therapeutic further comprises causing the one or more processors to:

obtain a scanned extrinsic label identifier from the labeled DCD;

verify the scanned extrinsic label identifier according to one or more similarity measures between the one or more digital assets associated with the digital token and the therapeutic hash digest; and verify the one or more parameters associated with the one or more ratios for the one or more lyophilized components according to the one or more similarity measures.

28. The computer-readable medium of claim 22, wherein authorizing autonomous access to the one or more lyophilized components further comprises controlling at least one rate of delivery with respect to at least one of the first chamber and the second chamber wherein the at least one rate of delivery is associated with one or more ratios.

29. The computer-readable medium of claim 28, wherein the at least one rate of delivery is associated with administration of the patient-specific therapeutic to the patient.

30. The computer-readable medium of claim 22, wherein the digital token comprises a digital representation of one or more of the following assets: patient data, diagnosis data, drug manufacturing data, lyophilization data, drug reconstitution data, drug administration data, a drug storage date, a drug shipping date, a point of care, a prescription, or a therapeutic outcome.

31. The computer-readable medium of claim 22, wherein the one or more lyophilized components comprise N-803 and at least one checkpoint inhibitor antibody.

32. The computer-readable medium of claim 22, wherein the one or more lyophilized components comprise N-803 and Bacillus Calmette-Guérin (BCG).

* * * * *